United States Patent [19]

Naskali

[11] Plant 4,859

[45] Jun. 22, 1982

[54] SANSEVIERIA PLANT

[75] Inventor: Richard J. Naskali, Moscow, Id.

[73] Assignee: Idaho Research Foundation, Inc., Moscow, Id.

[21] Appl. No.: 155,492

[22] Filed: Jun. 2, 1980

[51] Int. Cl.[3] ..... A01H 5/12

[52] U.S. Cl. ..... Plt./88

[58] Field of Search ..... Plt./88

*Primary Examiner*—Robert E. Bagwill

*Attorney, Agent, or Firm*—Wells, St. John & Roberts

[57] ABSTRACT

A new and distinct variety of Sansevieria plant that is a new chimeral cultivar formed as an adventitious bud on a leaf cutting of *Sansevieria trifasciata* var. *laurentii.* It has young leaves with narrow green margins and two broad yellow longitudinal bands flanking a central dull green core. The yellow bands become green after several months.

5 Drawing Figures

This invention is a new and distinct variety of Sansevieria plant.

The new variety, to be known as *Sansevieria trifasciata* 'Vandal Gold', originated from one adventitious bud formed at the basal end of a leaf segment of *Sansevieria trifasciata* var. *laurentii.* The leaf cutting was made by me in 1969; the unique growing shoot was subsequently discovered by me in the plants under my care in the Botany Greenhouses at the University of Idaho, Moscow, Idaho.

'Vandal Gold', the new variety, has been asexually reproduced by division of older plants of the new clone ("suckers"), and by induced growth of axillary buds along excised segments of the underground-growing rhizomes with scale-like leaves. This new variety does not reproduce true to the 'Vandal Gold' type via any leaf cuttings. No leaf cuttings of the 'Vandal Gold' have reproduced the new variety. Every specimen among some 50 plants derived from shoots or rhizome segments has reproduced true to the new variety.

The principal claim to novelty of this new variety resides in its (1) unique coloration pattern of foliage leaves from origin through maturity, (2) distinct diploid nature of the variegated foliage leaves, (3) value to the commercial trade for ornamental plants for home, indoor culture, (4) value of the unique greening characteristics of plastids to the study of the genetics and processes of photosynthesis and plastid development, and (5) its characteristic ability to be propagated only via rhizome sections with intact lateral buds, or by rhizome tips with intact terminal shoot apexes.

DESCRIPTION OF THE NEW VARIETY

Figure 2:
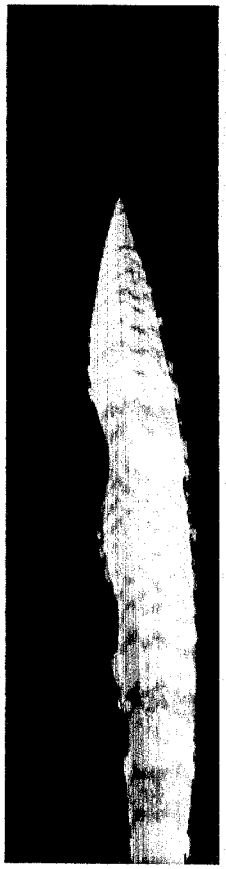
FIG. 2 is a photograph of a young leaf.
Figure 4:
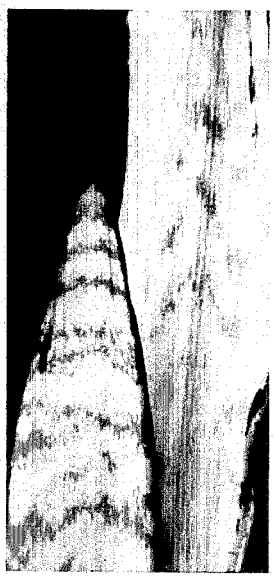
FIG. 4 is an enlarged photograph of a young leaf as seen in reflected light.
Figure 5:
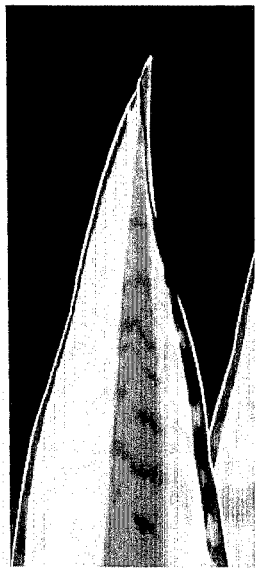
FIG. 5 is an enlarged photograph of a young leaf as seen in transmitted light.

Early in the growth of each aerial shoot of 'Vandal Gold' in a well lighted greenhouse, each foliage leaf is variegated in a yellow and green pattern (FIGS. 2, 4) which is unique to all Sansevierias known to me. Each young foliage leaf has a dark green margin; centripetal to the green margin is a yellow, elliptical population of mesophyll which, in turn, overlies a core of dark green cells, best viewed in transmitted light (FIG. 5).

Figure 1:
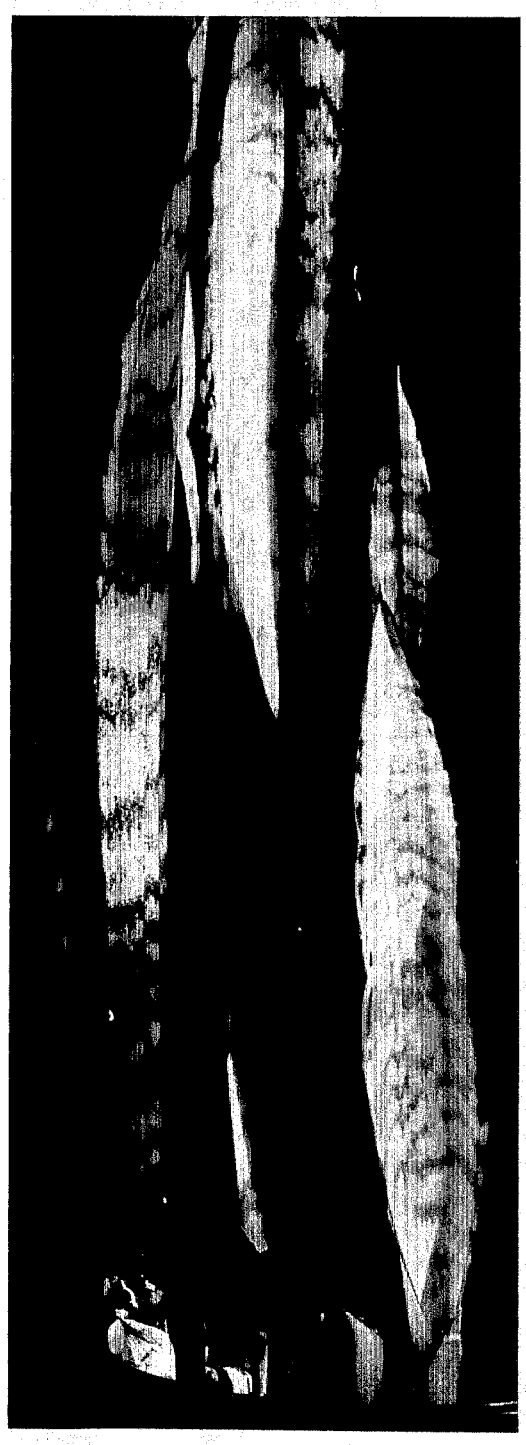
FIG. 1 is a photograph of a full plant.
Figure 3:
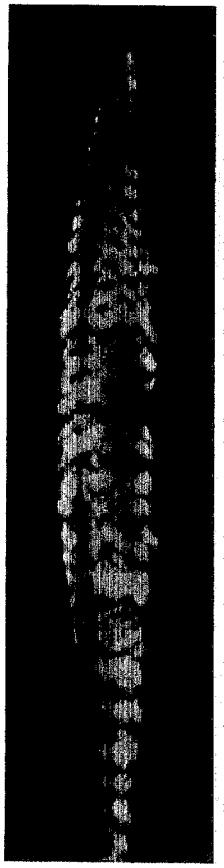
FIG. 3 is a photograph of an older leaf.

Greening and aging characteristics differ between the leaves of 'Vandal Gold' and *laurentii.* The tetraploid, yellow margins of *laurentii* do not become intensely green. By contrast, the yellow elliptical portion of diploid mesophyll of 'Vandal Gold' leaves, upon aging, becomes green (FIG. 3). I know of no other Sansevieria in which this phenomenon occurs to this degree. Growing plants of 'Vandal Gold' which have shoots of varying ages have a variety of phenotypically different leaves (FIG. 1). Old leaves of 'Vandal Gold' superficially appear as old leaves of the species, *Sansevieria trifasciata* var. *trifasciata.* The chimeral structure of 'Vandal Gold' persists, however.

Growth of the 'Vandal Gold' plants is as follows:

*Type.*—Upright, tall leaves in the form characteristic of *Sansevieria trifasciata* var. *trifasciata* and *Sansevieria trifasciata* var. *laurentii.*

*Rapidity.*—Grows and increases rapidly by means of rhizome tips or by rhizome sections which have lateral buds. Reproduces true to type only by means of rhizome tips and rhizome sections. Plants derived from rhizome sections are initially shorter than those derived from rhizome tips.

*Size.*—Plants growing in the University of Idaho Botany greenhouses have attained a size averaging 1.0 meter in height; occasionally, individual leaves become 1.3 meters tall. The tallest 'Vandal Gold' plants exceed the maximum height of the original species and the height of *laurentii.*

*Light conditions necessary to growth.*—Under greenhouse conditions plants attain their greatest variegation of young leaves. Under dim light conditions of indirect light from a north window under home culture, plants survive well, but do not have their most colorful yellowness of the leaf mesophyll; under such home conditions of dim light, 'Vandal Gold' plants are clearly distinguishable from other Sansevierias after one year of growth in my home.

*Drought tolerance.*—Plants of 'Vandal Gold', just as the other common varieties of *Sansevieria trifasciata,* survive well under dry home conditions. Plants survive for several weeks without watering, and yet they show no signs of withering or wilting. Plants grow well under conditions of low relative humidity.

*Flowers.*—'Vandal Gold', just as the progenitor clone (*Sansevieria trifasciata* var. *laurentii*), and the original species (*Sansevieria trifasciata*) flowers sporadically and profusely under growth conditions of the University of Idaho Botany Greenhouses. From thousands of flowers on dozens of inflorescences at various times of the year, no fruits or seeds have formed. Under Idaho greenhouse conditions, 'Vandal Gold' has been self sterile and cross sterile (when crossed with *Sansevieria trifasciata* var. *trifasciata* and *Sansevieria trifasciata* var. *laurentii*). This is not to be interpreted that 'Vandal Gold' is a self sterile plant; it is likely that Idaho greenhouse conditions are not promotive of its fruiting—for even the wild species does not fruit here. *Sansevieria trifasciata* var. *trifasciata* does form numerous fruits under conditions of Florida or some other sites.

Theoretically, 'Vandal Gold' would not reproduce with fidelity by seeds under any conditions, even if it did form seeds. By its presumed chimeral structure, 'Vandal Gold' could not be synthesized by seeds (sexual reproduction) in any manner again with highest probability. Theoretically, if any seeds did form after self pollination of 'Vandal Gold', the progeny should have a homogeneous genotype, most probably with defective plastids that could yellow with ageing. The chance of 'Vandal Gold' being synthesized again and spontaneously via seeds is extremely remote—and then it would require very specific mutation(s) in very specific sites in shoot apexes or embryos.

*Color.*—When viewed in reflected overcast daylight, the leaves of the new variety have alternating transversely banded segments of silvery green or silvery yellow and yellow or green. Using color numbers and names from R.H.S. Colour Chart (The Royal Horticultural Society, London, U.K.) evaluations of colors from adaxial surfaces midway along the length of representative young leaves showed an outer leaf margin of alternating areas of 191 C or D (Greyed-green group) and 139 A (Green group). These areas respectively abut midportion transverse bands of 145 C (Yellow-green group) and 151 B (Yellow-green group). An upright central band along each leaf has corresponding areas of 148 D (Yellow-green group) and 144 A (Yellow-green group). Older leaves, when similarly evaluated for color, exhibited alternating transverse bands of 139 C (Green group) and 137 B (Green group).

Comparisons with other known, patented Sansevierias

In size, shape, and coloration, Sansevieria 'Vandal Gold' leaves and plants are larger and differently colored than the varieties in any of the following U.S. Plant Pat. Nos. 470, 633, 1,220, 1,221, and 1,224. These are dwarf plants which are not known to flower. 'Vandal Gold' plants flower profusely periodically through the year.

'Vandal Gold' plants have broad leaves with two vertical strips of yellow when they are young; the yellow strips disappear as the leaves age and the plastids become green. By contrast, leaves of Bantel's Sansevieria (U.S. Plant Pat. No. 796) are narrower and shorter than those of 'Vandal Gold'; Bantel's Sansevieria leaves have many white vertical strips which do not become green with age.

Comparisons with other known Sansevierias

'Vandal Gold' Sansevierias have longer, differently colored leaves than leaves of Sansevieria 'Futura' and 'Craigii'. The short, wide leaves of 'Futura' have very narrow yellow margins which do not become green in the Idaho Botany Greenhouse.

'Craigii' Sansevierias have short leaves (circa 18 inches, or 45 cm) which grow in a divergent, arching orientation away from the vertical. By direct comparisons of living plants of 'Vandal Gold' and 'Craigii', it is clear that 'Craigii' is not easily confused with 'Vandal Gold'. 'Craigii' leaves do not consistently have narrow green margin; the yellow portions of the leaf blade are irregularly sized and spaced; the yellow portions of 'Craigii' do not become characteristically green upon ageing. On some occasions, one lateral half of a 'Craigii' leaf can be solid green. In another stark contrast with 'Vandal Gold', plants of 'Craigii' grow very slowly, and are easily damaged by bright sunlight. In addition, the leaves of 'Craigii' have not formed any of the silvery and irregular transverse banding that characterizes 'Vandal Gold'.

The shape and size of the leaves of the new 'Vandal Gold' plants are similar to the shapes and sizes of *Sansevieria trifasciata* var. *trifasciata* and *Sansevieria trifasciata* var. *laurentii.*

Some leaves of 'Vandal Gold' are larger than the typical *Sansevieria trifasciata* with reference to length and width. Usually plants of 'Vandal Gold' have wider and somewhat longer leaves than the typical *Sansevieria trifasciata* var. *laurentii.*

Extensive cytological investigations have demonstrated that cells of 'Vandal Gold' leaves are all diploid, unlike its progenitor *laurentii* (which has tetraploid and diploid cells in each of its foliage leaves). Whereas *laurentii* shoot apexes are all cytochimeras, shoot apexes of 'Vandal Gold' are chimeral, but not cytochimeras.

Sansevieria trifasciata var. *laurentii* have long been known to be a chimeral plant which has two different genotypes in each shoot apex and leaf. Each *laurentii* shoot apex has a tetraploid outer mantle layer which coincidentally has defective plastids. All other parts of *laurentii* shoot apexes are constituted of diploid cells with typical greening characteristics attributable to typical plastids (proplastids and chloroplastids).

Leaves of *laurentii* have tetraploid, yellow leaf margins and epidermis surrounding a diploid, normal-greening core of mesophyll. All non-vascular mesophyll which was derived from the second and subjacent cells of shoot apexes of *laurentii* is diploid and green.

The presumed original, wild progenitor of *laurentii, Sansevieria trifasciata* var. *trifasciata,* has diploid cells and normal-greening plastids throughout shoot apexes and leaves.

The features of 'Vandal Gold' which make it unique and valuable are as follows:

(1) The coloration pattern of leaves with narrow green margins and two broad yellow bands flanking a central dull green core.

(2) The variegated color effect in a growing plant provided by the progressive changes in the yellow bands as they become green.

(3) This highly ornamental variegated Sansevieria adds to the numerous Sansevierias in the commercial trade for house plant use.

(4) Periclinal chimeras with shoot apexes organized into two or more genetically different cells are rare among the monocotyledonous plants. In addition to the *Sansevieria trifasciata* var. *laurentii,* the new 'Vandal Gold' provides another of the most powerful tools available to developmental anatomists for discovering patterns of leaf, stem, and shoot apex ontogeny. In contrast to var. *laurentii* in which the defective plastids are located in the outermost mantle layer of the shoot apexes, 'Vandal Gold' appears to have its defective plastids in the shoot apex limited to the second mantle layer.

(5) Unique greening characteristics of aging leaves of 'Vandal Gold' provide researchers of plastid ontogeny and researchers of photosynthesis with a valuable tool with which to study developmental physiology, anatomy, cytology, and genetics. At their oldest and greenest state, the defective plastids appear to be unique among plastids thus far investigated.

I claim:

1. A new and distinct variety of Sansevieria plant substantially as shown and described.

* * * * *